(12) United States Patent
Greenwald et al.

(10) Patent No.: US 8,049,517 B2
(45) Date of Patent: Nov. 1, 2011

(54) SENSOR AND METHOD FOR DETECTING A SUBSTANCE

(75) Inventors: Shlomo Greenwald, Ithaca, NY (US);
Zipora Greenwald, Ithaca, NY (US);
Uri Moshe Greenwald, Ithaca, NY (US)

(73) Assignee: Greenwald Technologies, LLC, Ithaca, NY (US)

( * ) Notice: Subject to any disclaimer, the term of this patent is extended or adjusted under 35 U.S.C. 154(b) by 503 days.

(21) Appl. No.: 12/334,980

(22) Filed: Dec. 15, 2008

(65) Prior Publication Data

US 2009/0153148 A1    Jun. 18, 2009

Related U.S. Application Data

(63) Continuation-in-part of application No. 11/735,784, filed on Apr. 16, 2007, now Pat. No. 7,482,818.

(60) Provisional application No. 60/744,951, filed on Apr. 17, 2006.

(51) Int. Cl.
*G01R 27/32* (2006.01)
*G01N 27/00* (2006.01)
*G01S 13/08* (2006.01)

(52) U.S. Cl. ........ 324/639; 324/640; 324/71.1; 342/124

(58) Field of Classification Search .................. 324/639, 324/640, 71.1; 342/124
See application file for complete search history.

(56) References Cited

U.S. PATENT DOCUMENTS

| | | | |
|---|---|---|---|
| 4,419,622 A * | 12/1983 | Cuneo et al. | 324/629 |
| 4,782,282 A | 11/1988 | Bachman | |
| 5,351,036 A | 9/1994 | Brown et al. | |
| 6,169,394 B1 | 1/2001 | Frazier et al. | |
| 6,691,563 B1 | 2/2004 | Trabelsi et al. | |
| 7,053,629 B2 * | 5/2006 | Nevermann | 324/644 |
| 7,068,050 B2 | 6/2006 | Steele et al. | |
| 7,378,849 B2 * | 5/2008 | Weatherall et al. | 324/321 |
| 7,796,684 B2 * | 9/2010 | Trott | 375/219 |
| 2004/0119637 A1 | 6/2004 | Angal et al. | |

OTHER PUBLICATIONS

Jackson, "Classical Electrodynamics", Hole in Dielectric, 1975 (p. 152).
Jackson, "Classical Electrodynamics", Hole in Dielectric, 1975 (p. 151).
Nathan Ida, Engineering Electromagnetics., 2000 pp. 1128-1137; Springer-Verlag, New York.

* cited by examiner

*Primary Examiner* — Melissa Koval
*Assistant Examiner* — Daniel Miller
(74) *Attorney, Agent, or Firm* — Brown & Michaels, PC

(57) ABSTRACT

A sensor for detecting a substance in a physical space, having an RF energy emitter fed by a signal source on one side of the space and an RF energy receiving element coupled to a detector at an opposite side of the channel, spaced apart by a distance (r) selected so that when the signal wavelength (λ) changes based on the value of the dielectric constant (∈) of the particular substance in the physical space between the emitter and receiver, the mode of field type within the sensor channel changes between near field and intermediate or far field mode.

20 Claims, 14 Drawing Sheets

SENSOR AND METHOD FOR DETECTING A SUBSTANCE

REFERENCE TO RELATED APPLICATIONS

This application claims one or more inventions which were disclosed in Provisional Application No. 60/744,951, filed Apr. 17, 2006, entitled "Liquid/Air Bubble/Solid Objects Detector." The benefit under 35 USC §119(e) of the United States provisional application is hereby claimed, and the aforementioned application is hereby incorporated herein by reference.

This is a continuation-in-part of co-pending patent application Ser. No. 11/735,784, entitled "SYSTEMS AND METHODS FOR DETECTING THE PRESENCE AND/OR ABSENCE OF A SOLID LIQUID OR GAS", filed Apr. 16, 2007. The aforementioned application is hereby incorporated herein by reference.

BACKGROUND OF THE INVENTION

1. Field of the Invention

The present invention relates generally to the field of automated sensing systems and methods. More specifically, the present invention is directed to systems and methods for detecting the presence and/or absence of a substance (solid, liquid, gas, or mixture thereof), utilizing an RF energy emitter and RF energy receiver/detector for determining whether a substance is present within a defined physical space between the RF energy emitter and RF energy receiver/detector.

2. Description of Related Art

A wide variety of conventional systems and methods are available for determining whether a solid or liquid is present within a specified physical space utilizing an RF emitter and RF energy detector.

In US patent number 2004/0119637 Angel et al. describe a sensor that utilizes changes in the impedance of a transmission line to determine whether an ink cartridge has run out of ink.

U.S. Pat. No. 6,691,563 by Trabelsi et al. gives a method using a calibration equation to calculate the degree of moisture in particulate matter. In their method, the degree of RF signal attenuation is measured when passed through particulate matter and this is one of the factors used to derive moisture content.

Both U.S. Pat. Nos. 4,727,311 and 4,674,325 by Walker and Kiyobe et al. respectively transmit a microwave signal via horns to measure moisture.

U.S. Pat. No. 7,068,050 by Steele et al. measure the degree of attenuation of signal transmitted by a near field effect to determine the moisture content of lumber. This device operates strictly in the near field.

SUMMARY OF THE INVENTION

In accordance with various embodiments of the present invention, systems and methods are described for detecting a substance, utilizing an RF energy transmitted from an emitter to a receiver/detector spaced apart by a determined distance which is selected based upon the wavelength of the energy. More specifically, an RF energy emitter fed by a signal source is provided on a first side of a physical space and an RF energy receiving element coupled to a detector is provided at an opposite side of the channel, spaced apart by a distance (r).

The RF energy has a characteristic frequency, which in turn has a wavelength ($\lambda$) which changes when it passes through the particular substance present in the physical space between the RF energy emitter and the RF energy receiving element. The change to the wavelength ($\lambda$) is determined by the value of the dielectric constant ($\in$) of the particular substance the RF energy passes through. As will be discussed in greater detail in the detailed description of the invention below, the relationship between distance (r) and wavelength ($\lambda$) will determine whether energy is coupled from the emitter to the receiver in near field mode, intermediate field mode or far field mode.

According to the teachings of the invention, the distance (r) between emitter and receiver is selected so that when the signal wavelength ($\lambda$) changes based on the value of the dielectric constant ($\in$) of the particular substance in the physical space between the emitter and receiver, the mode of field type within the sensor channel changes between near field and intermediate or far field mode. The change in field mode causes either an increase or decrease in signal power, depending on the type of change.

Additionally, when the sensor is operating in intermediate field or far field mode, a measurement of received signal strength can be used to discriminate between different substances present in the physical space.

As used in this description, it will be understood that the term "substance" means a solid, liquid or gas, or a mixture of solid with liquid, liquid with gas, solid with gas, or a mixture of different solids, liquids or gasses in a single phase. The term "detecting" means detecting the presence of a substance, the absence of a substance, or a change in composition of the substance (i.e. liquid to gas, solid to liquid, one kind of liquid to another, etc.).

DETAILED DESCRIPTION OF THE INVENTION

Figure 1:
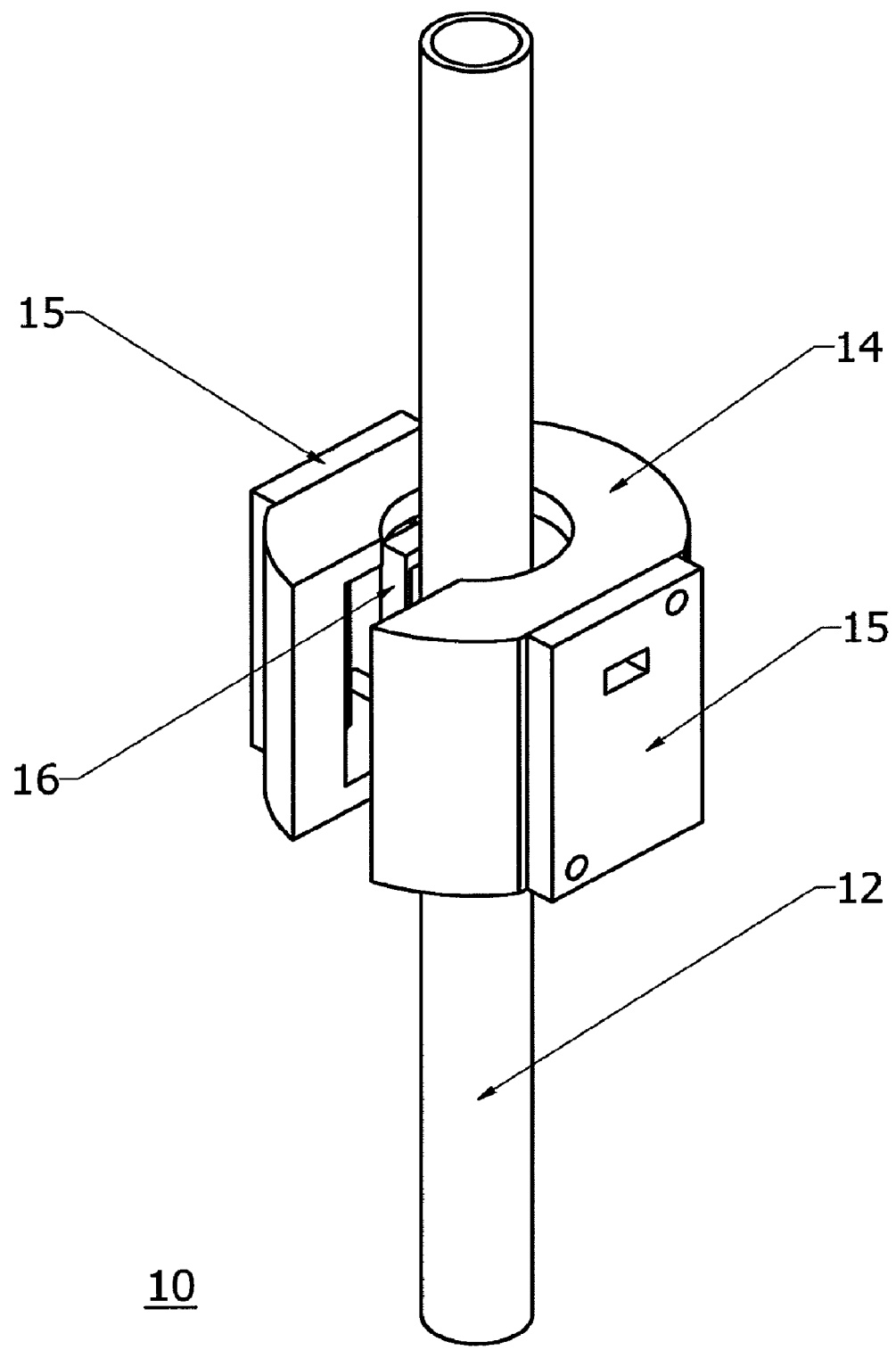
FIG. 1 illustrates a first exemplary embodiment of the present invention utilizing the RF source and the RF detector elements.

In order to define the boundaries of the field mode within the sensor—near field mode, intermediate field mode or far field mode—we take the term ($\beta r$) from the equations for electric and magnetic field intensities for a dipole antenna expressed in Eq. 1 and Eq. 2 respectively. In these equations ($\beta$) is the wave number and is given by $\beta=2\pi/\lambda$. The terms $\alpha$, $\alpha 2$, and $\Phi$ incorporate the remainder of the terms in these well known equations for the purpose of simplification.

$$E = -(\alpha)\cos\theta(1/[(\beta)(r)]^2 + 1/[(\beta)(r)]^3) - (\alpha 2)\sin\theta(1/(\beta)(r) + 1/[(\beta)(r)]^2 + 1/[(\beta)(r)]^3) \quad \text{(Eq 1)}$$

$$H = -(\Phi)\sin\theta(1/(\beta)(r) + 1/[(\beta)(r)]^2) \quad \text{(Eq 2)}$$

In a near field, where $(\beta)(r) \ll 1$, the electrical field component—which is the dominant component in the near field—decays at a rate of $1/r^3$, and the magnetic field component is nearly nonexistent so there is no wave propagation in this field. Because of the relatively rapid rate of decay, lack of wave propagation, and the dipole antenna being driven by very low power—on the order of a few milliwatts—the received signal is extremely low when there is a near field type within the sensor channel.

In either an intermediate or far field, where $(\beta)(r) > 1$ or $(\beta)(r) \gg 1$ respectively, the rate of field decay is no longer $1/r^3$ but is $1/r^n$ where $1 < n < 2$ in the intermediate field and $n=1$ in the far field. In these fields there is presence of both a magnetic and electric field component so wave propagation occurs. In this case the dipole antenna radiates power according to its Radiation Resistance parameter which is proportional to $\sqrt{\in}$, and the reciprocity theorem states the efficiency of the receiving antenna is also enhanced by a factor of $\sqrt{\in}$. Due to these enhancements in signal power as well as the lesser rate of decay, there is a strong increase in signal seen by the RF energy detector when there is either an intermediate or far field type within the sensor channel.

In the sensor the operating frequency and distance (r) are set in such a way that the ($\in$) value of a particular substance present in the channel will determine enough of a change in wavelength ($\lambda$) so that the type of field in the channel will change from the type of field it was before the particular substance was present in the channel to a different type of field with different properties. The change in wavelength ($\lambda$) is a known phenomenon where the RF experiences a phase velocity decrease of $1/\sqrt{\in}$ and therefore a wavelength decrease of $\lambda/\sqrt{\in}$ when the RF energy passes through a dielectric. A change from $(\beta)(r) < 1$ to either $(\beta)(r) > 1$ or $(\beta)(r) \gg 1$ will bring about a marked increase in signal to the RF energy detector, and a change from $(\beta)(r) > 1$ or $(\beta)(r) \gg 1$ to $(\beta)(r) < 1$ will bring about a marked decrease in signal to the RF energy detector.

Additionally, once the presence of a particular substance in the channel causes the field type to become an intermediate or a far field, further measured changes in signal strength while remaining in the intermediate or far field represents the subsequent immediate presence of a new substance. These signal strength changes are due to Radiation Resistance and the reciprocity theorem.

Those of ordinary skill in the art will appreciate that a wide range of frequencies and distances (r) are possible for utilization in conjunction with the systems and methods of the present invention.

In accordance with the preferred exemplary embodiment, the RF energy emitter and RF energy receiver structures are preferably located within a housing that is comprised of a conductive material, or which is shielded with conductive material for the purpose of limiting spurious emissions from the device. The shielded structure also limits extraneous RF noise thereby improving accuracy and the ability of the system to achieve finer resolution. Although any conductive housing is suitable for providing the shielding structure, in order to reduce manufacturing costs, it is preferred that the housing is embodied as a plastic structure having internal sidewalls coated with a material such as, for example, chrome. It should be recognized that other conductive materials will also be suitable and it is preferred that the thickness of the conductive shielding member be at least approximately a few skin depths at the primary RF emission frequency. Machined aluminum may also be used for the housing.

In accordance with a first preferred exemplary embodiment of the present invention, a simple RF diode detector such as, for example, a Schottky diode is utilized for determining whether or not a substance is present in the channel between the RF energy emitter and the RF energy receiver/detector. In such an embodiment, a comparator is preferably used for providing an appropriate signal level triggering point for ascertaining whether or not the substance is present in the channel between the RF energy emitter and RF energy receiver/detector. Alternatively, instead of utilizing a simple diode mechanism, a commercial RF detector may be utilized and the output of this RF detector is transmitted to a comparator with an appropriate comparison signal level for ascertaining the presence and/or absence of a substance within the channel between the RF energy emitter and RF receiver/detector.

There is a very wide range of applications for the systems and methods described herein which are able to determine whether a substance passes through the space between the RF energy emitter and RF energy receiver/detector. Applications for these types of alternate embodiments include automated systems which may be used for counting passed objects, for measuring flow rate, for measuring the point a liquid product ceases dispensing, and for identifying the presence of a new solid, liquid, or gas component added to a liquid.

In one embodiment the sensor can be used for counting the passage of solid objects such as pills. It can be easily and inexpensively incorporated into a pill dispensing system for highly accurate counting and sensing of object passage. Currently, an optical sensor is the most common conventional solid product detector. The optical sensor is extremely sensitive to dust build up, which regularly occurs and causes malfunction. These optical sensors require periodic stoppage of the packaging process in order to allow for cleaning, which carries a heavy cost in terms of packaging efficiency.

In another embodiment the device may be used as a highly accurate flow sensor. One such implementation is in a urine flow measuring device for use in monitoring the urine outputs of patients. There is a great need for such devices since at present this type of monitoring is performed manually and is highly error prone. A second implementation is for an effective and relatively inexpensive flow determining device for intravenous infusion systems which will allow hospital staff to set the desired flow rate and alarm the staff when there is no flow (for example; the patient is pinching the tube) or the infusion liquid bag is empty or out of product. At present, hospitals utilize expensive infusion pump systems in order to carry out these functions.

Another embodiment is an out of product sensor. In post-mix beverage dispensers where it is desired to know when the bag of the concentrated liquid beverage is out of product there may be a need to sense fluid levels and/or the presence or absence of the product, the sensor can alarm when flow has ceased. Currently, in typical conventional post-mix dispensers, a vacuum sensor is typically used to detect when the concentrate liquid bag is out of product. The currently used vacuum sensor is inferior because it is required to come into direct contact with the beverage concentrate liquid, it works only in systems where the concentrated liquid dispensing pump is powerful enough to create a vacuum when the bag is out of product, and it has a long response time during which only water is dispensed.

In yet another alternate embodiment, the sensor is able to identify the presence of a new solid, liquid, or gas component added to a liquid. This can be used in intravenous infusion to detect a potentially fatal air bubble. In this alternate embodiment, the patient infusion system preferably includes a processor or controller and a small, solenoid operated pinch valve and alarm. In this embodiment, when the system detects an air bubble equal or larger to the allowed volume it will activate the pinch valve which will pinch the infusion tubing and stop the flow. The system also preferably activates an alarm. In addition the air-bubble device will be able to measure the total accumulated air bubble volume, when each one of them is smaller than the critical volume, administrated to the patient during the time of the infusion.

Some advantages of this embodiment include:
Low cost;
Small size;
Low power requirement
Because it is small in size the system can be mounted directly on the infusion pole and easily moved with the patient.

In a second implementation of the same embodiment, the systems and methods of the present invention may be used in conjunction with dialysis machines. Specifically, the substance sensor of the present invention can be used in dialysis systems to detect the presence of gas bubbles or solids in the recirculated blood.

Those skilled in the art will appreciate that there are a wide variety of other applications for the substance detection systems and methods of the present invention.

FIG. 1 illustrates a first preferred exemplary embodiment of the present invention, which is shown generally at 10. In this first preferred exemplary embodiment, a tube member 12, preferably comprised of a nonconductive material such as plastic, and the like, provides a transmission channel for a substance (solid, liquid, gas or mixture thereof).

An RF energy emitter/receiver structure housing 14 preferably surrounds or at least substantially surrounds the tube member 12. In illustration of FIG. 1, the housing 14 is a C-shaped generally cylindrical body located around the tube member 12. The RF energy emitter/receiver structure housing 14 may be comprised of a conductive material such as machined aluminum or any other conductive structure and is preferably comprised of molded plastic with a coating of chrome on the internal side walls of plastic material. The conductive housing limits spurious emissions from the device and reduces extraneous RF noise thereby improving accuracy and the ability of the system to achieve finer resolution. It should be recognized by those skilled in the art at that an alternate two-piece construction or multiple piece construction could be provided, which simply snap fits over the nonconductive tube member 12.

The RF energy emitter/receiver structure housing 14 is preferably provided with access plates 15 on opposed sides of the RF energy emitter/receiver structure housing 14. The opening in the housing structure 14 also provides a view of the RF energy emitter structure 16 which is described in more detail below.

Figure 2:
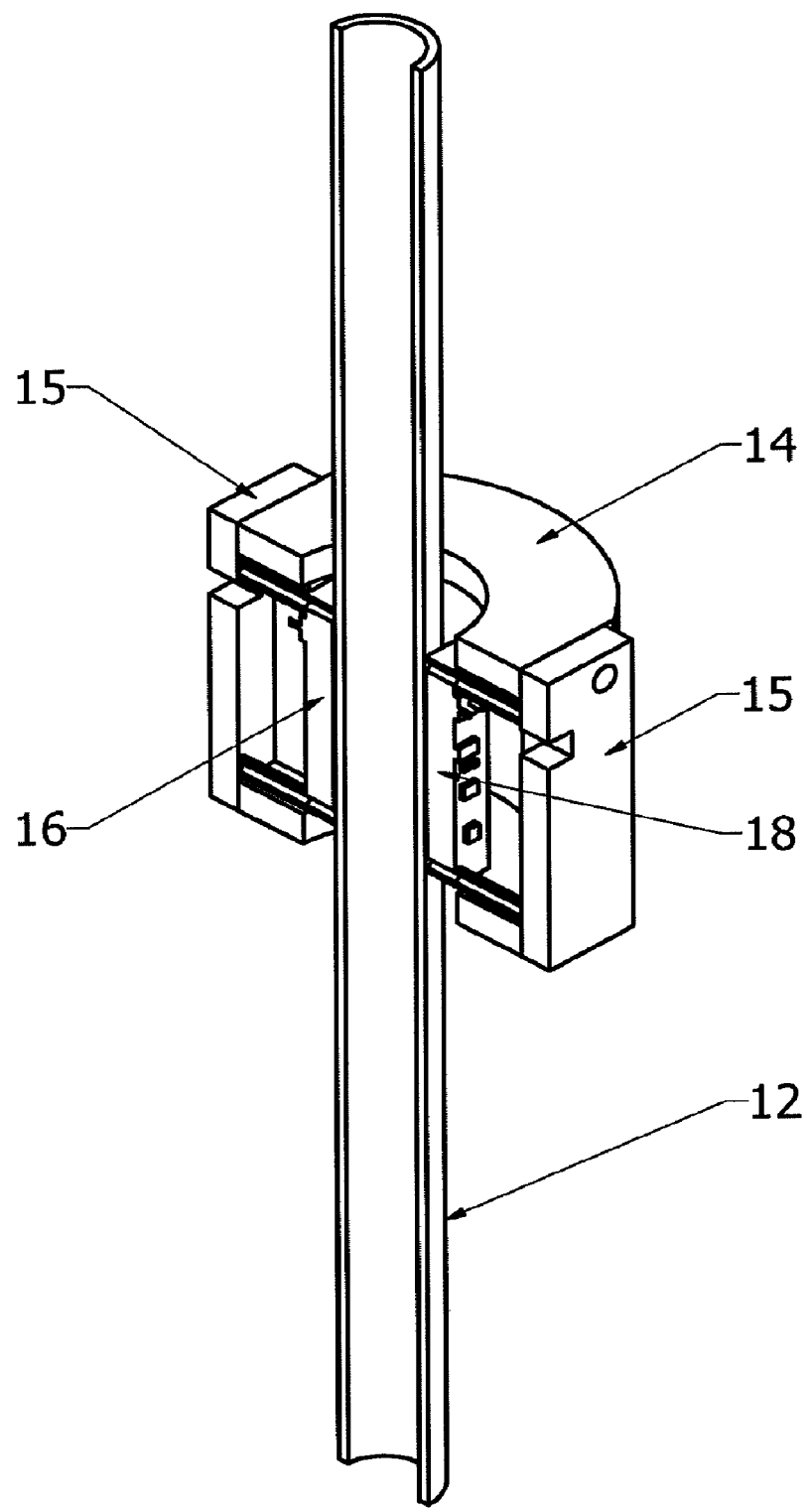
FIG. 2 illustrates a cutaway side view which illustrates the RF source and the RF detector elements of FIG. 1.

FIG. 2 is a cutaway illustration of the RF energy emitter/receiver structure housing 14 and the nonconductive tube member 12, which shows the relationship between the non-conductive tube member 12 as well as the RF energy emitter 16 which is provided on a first side of the substance transmission channel 12 and an RF energy receiver/detector 18 that is provided at an opposite side of the substance channel 12.

The RF energy emitter 16 either continuously or periodically emits RF energy which in the preferred exemplary embodiment is in the high-frequency or more preferably ultrahigh frequency signal range. For example, in exemplary embodiment, the RF energy transmission source 16 provides at least a primary output of approximately 2.4 GHz. Those of ordinary skill in the art will appreciate that a wide range of transmission frequencies are possible for utilization in conjunction with the systems and methods of the present invention. The RF energy receiver/detector mechanism 18 is located across the transmission channel.

Additional circuitry is provided either within the housing 14 or remotely from the housing 14 which provides a signal indicative of whether a substance is present within the space between RF energy emitter 16 and the RF energy receiver/detector 18. This is possible due to the fact that the inventors have discovered that an amount of RF energy transferred from the RF energy emitter 16 structure to the RF energy receiver/detector 18 is altered depending upon whether or not a substance is located between RF energy emitter 16 and the RF energy receiver/detector 18.

Circuitry which is described in more detail below is provided for ascertaining whether or not a substance is located between RF energy emitter 16 and the RF energy receiver/detector 18. In accordance with the preferred exemplary embodiment, a comparator is preferably utilized in making this determination. More specifically, a voltage corresponding to an amount of detected RF energy is provided and compared with a predetermined triggering or voltage reference level. Those skilled in the art will appreciate that there is an effect on signal power transferred from the RF energy emitter 16 to the RF energy receiver/detector 18 determined by the type of substance located in the channel. Selection of an appropriate reference level input to the comparator is utilized in making the determination as to whether or not a substance is located between RF energy emitter 16 and the RF energy receiver/detector 18.

For example, in an embodiment wherein the system is utilized as an out of product sensor, logic circuitry is provided to indicate that a fluid is no longer present. This can easily be achieved due to the presence of fluid in the sensor channel being replaced with air when product flow has ceased. Then there will be a recognition that the transferred RF energy will decrease and therefore the voltage corresponding to the amount of detected RF energy will fall below a predetermined level indicating that the fluid is no longer present between the RF energy emitter 16 and the RF energy receiver/detector 18. The same signal relationship will exist (i.e. a decreasing signal voltage trigger point) when the system is used as a bubble detector for identifying potentially harmful bubbles in intravenous fluid lines. Alternatively, when the system is used as a pill counter, for example, changes in the amount of detected RF energy and corresponding variations in the output voltage from the RF detector can be used to determine when a pill or other solid object passes between the RF energy emitter 16 and the RF energy receiver/detector 18.

In most applications the RF source and RF detector are on all the time and a microprocessor is used to analyze the output signal from the RF detector. The microprocessor can either samples the detector output signal at a rate of 100 to 300 Hz. depend on the application or in a continuous manner In situations where it is desired to increase the sensitivity of the measurements (when the output signal from the RF detector is small and the noise level is changing randomly) the detector will stay on all the time while the RF source will be modulated at 50% duty cycle where the time of one cycle is smaller or equal to the signal width. During the time when the RF source is off, the detector will measure the noise level while during the time of the cycle when the RF source is on, the detector will measure the signal plus the noise. By subtracting the measured signal during the time the RF is off from the measured signal when the RF is on, it is possible to calculate the value of the signal level only. For example; if the signal width is 100 msec it is preferred to modulate the RF source at 50% duty cycle 50 msec on and 50 msec off.

Accordingly, those skilled in the art will appreciate that various signal processing arrangements may be provided in different types of applications for determining whether a substance is present at a specified location. Those skilled in the art will also appreciate that either logic circuitry or a microprocessor may be utilized for determining whether an output signal corresponding to the amount of detected RF energy is above or below a predetermined threshold. As noted, depending upon the particular implementation this information can be used to determine whether or not a variety of different events have occurred.

FIG. 3A illustrates a perspective view of an exemplary circuit board for use conjunction with the present invention. In the preferred exemplary embodiment, the RF energy emitter 16 and at least most of its required circuitry 22 is formed on a single printed circuit board. The same is also true of the RF energy receiver/detector 18 as at least most of its required circuitry 22 is formed on a single printed circuit board.

More specifically, as shown in FIG. 3A, the RF emitter 16 preferably includes an appropriately tuned oscillator including all of the necessary transistors, capacitors and resistors 22 on a first side of the print circuit board as shown in FIG. 3A. It should be recognized that the subject matter illustrated in FIGS. 3A-D applies to both the RF energy emitter 16 and the RF energy receiver/detector 18. The illustrations of FIGS. 3A-D are meant to be generic illustrations of either the RF energy emitter 16 or the RF energy receiver/detector 18.

FIGS. 3A and 3B also illustrates a connector 24 which in the preferred exemplary embodiment is used to provide power and ground connections or any other appropriate voltage levels as well as a signal output.

It should also be recognized that it is not necessary to have at least most of the circuitry associated with the RF energy emitter 16 and the RF energy receiver/detector 18 on their respective printed circuit boards. As detailed below, a coaxial cable may physically connect a separate RF source to the actual emitter structure and the RF energy receiver can be connected to the RF detector via a similar coaxial cable.

A via or through hole connection is preferably provided in the print circuit board to transmit the RF energy from a first side of the circuit board at which the transistors, capacitors and resistors 22 are located to an opposite side thereof. The same is also true for the RF receiver/detector when the detector circuitry is physically located on the same circuit board as the RF energy receiving element. FIG. 3B illustrates a top plan view of an exemplary circuit board for use in conjunction with the present invention which illustrates the transistors, capacitors and resistors 22. FIG. 3C illustrates a side view of an exemplary circuit board for use in conjunction with the present invention. FIG. 3D illustrates an antenna or electromagnetic energy emitter or receiver portion 25 provided on a printed circuit board for use in conjunction with the present invention. The antenna or electromagnetic energy emitter or receiver portion 25 is conveniently formed as a conductive metal layer on the other side of the circuit board. In the preferred exemplary embodiment, the circuit board is preferably approximately 0.3 by 0.9 inches. The electromagnetic energy emitter or receiver portion 25 is preferably 0.3×0.7 inches.

Figure 4:
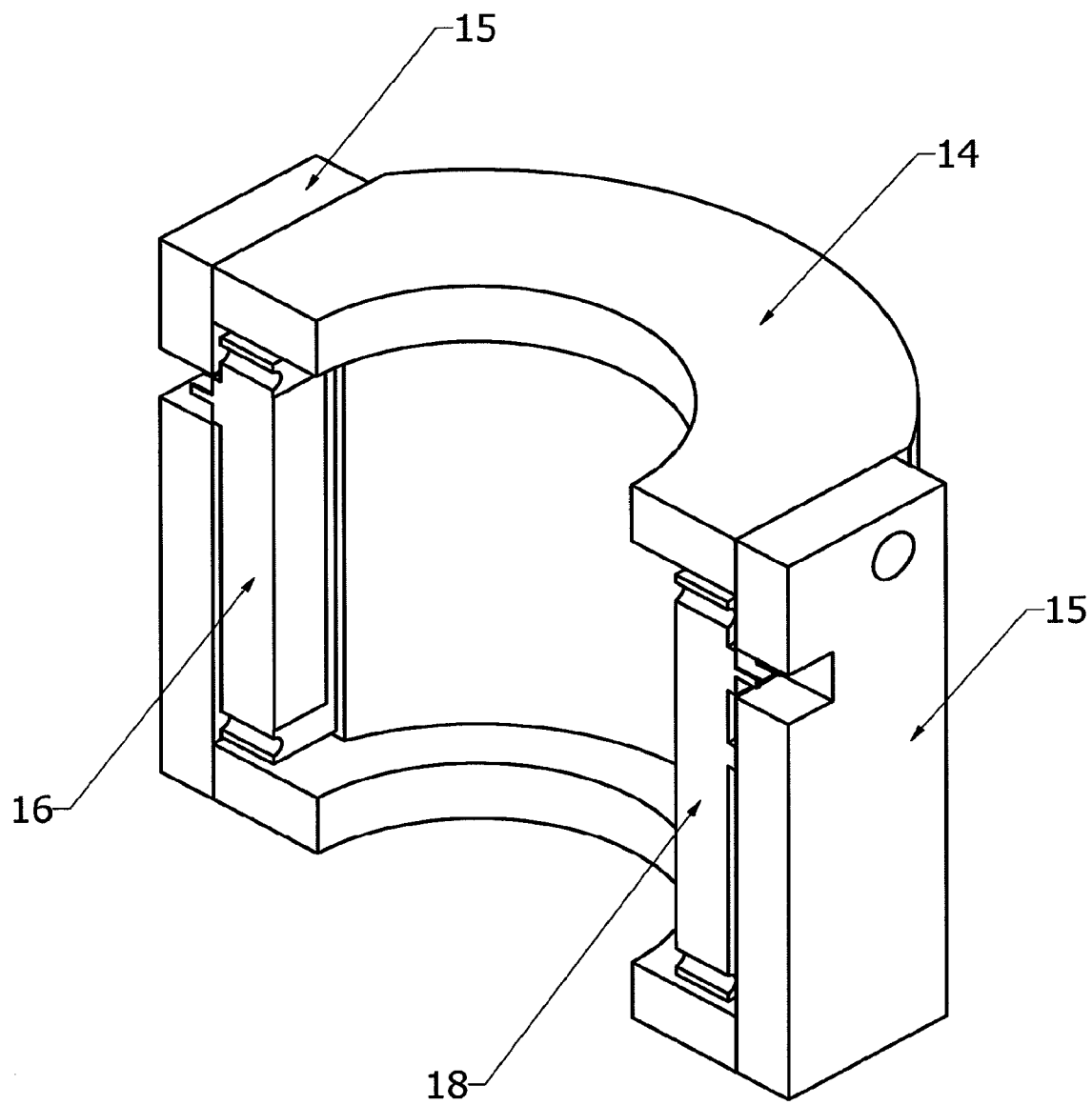
FIG. 4 illustrates the details of an exemplary RF emitter and RF receiver/detector assembly enclosed within its cavity.

FIG. 4 is a cutaway illustration of the RF energy emitter/receiver structure housing 14 and the RF energy emitter 16 and the RF energy receiver/detector 18. FIG. 4 illustrates in detail the preferred relative physical relationship between the RF energy emitter 16 and the RF energy receiver/detector 18. More specifically, the RF energy emitter 16 and the RF energy receiver/detector 18 are preferably diametrically opposed across the physical space within which the substance to be detected is transmitted.

It should be recognized that the substance sensing systems and methods of the present invention do not rely upon a single emitted signal wavelength or channel diameter. Rather, for every particular embodiment the wavelength ($\lambda$) and distance (r) are calculated and set using the value of ($\in$) of the substance to be detected, in order to create the change of field mode within the channel that occurs with the presence of a substance in the space between the RF energy emitter 16 and the RF energy receiver/detector 18.

When the field within the sensor channel is made an intermediate or a far field by presence of a particular substance, further changes in ($\in$) resulting from changes in the substance will cause an increase or decrease in signal power depending on whether ($\in$) increases or decrease respectively. Using this change in signal strength, which can be detected using signal strength measurement, changes in the composition of the substance (or from one substance to another) can be detected.

Figure 5:
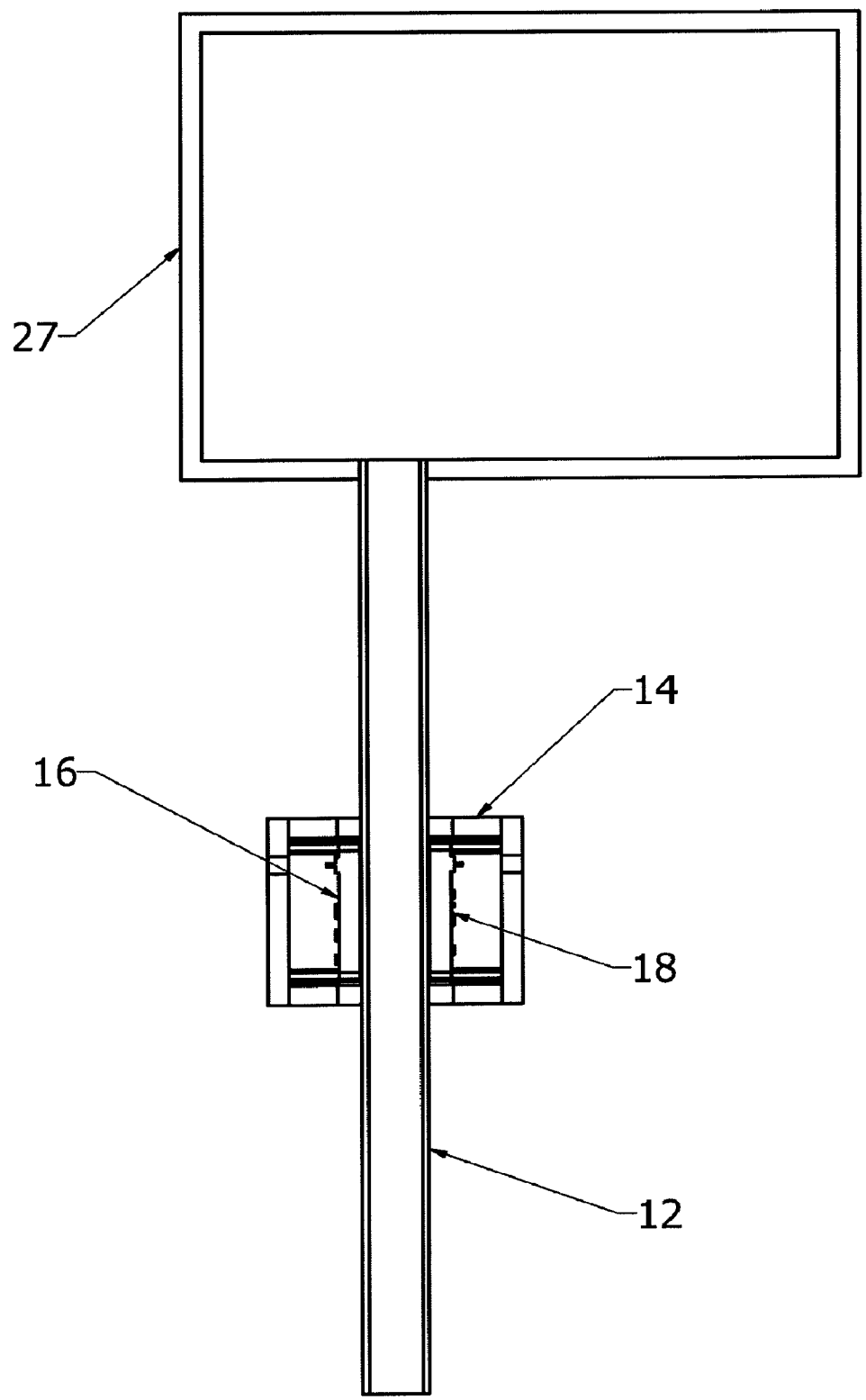
FIG. 5 illustrates use of the RF emitter and RF receiver/detector as an out of product sensor.

FIG. 5 illustrates an exemplary embodiment of the present invention wherein the RF emitter 16 and the RF energy receiver/detector 18 are employed as an out of product sensor in a vending machine system. For example, this arrangement may be utilized in determining when a coffee machine or soda machine is either running out of or which has run out of the concentrated product to be dispensed.

In this embodiment, the RF energy emitter 16 and the RF energy receiver/detector 18 are secured with a fluid transmission channel 12 located there between. The fluid transmission channel 12 is connected to a product containment structure 27. As described above, a change in the coupled RF energy between the RF energy emitter 16 and the RF energy receiver/detector 18 is used in determining if the product containment structure 27 no longer contains fluid. Either a microprocessor or logic circuitry may be used to generate an appropriate electrical signal when this occurrence is determined. This signal may be transmitted to a remote location via an RF transmitter or a network connection so that the containment structure 27 may be replenished or replaced at an appropriate time.

Figure 6:
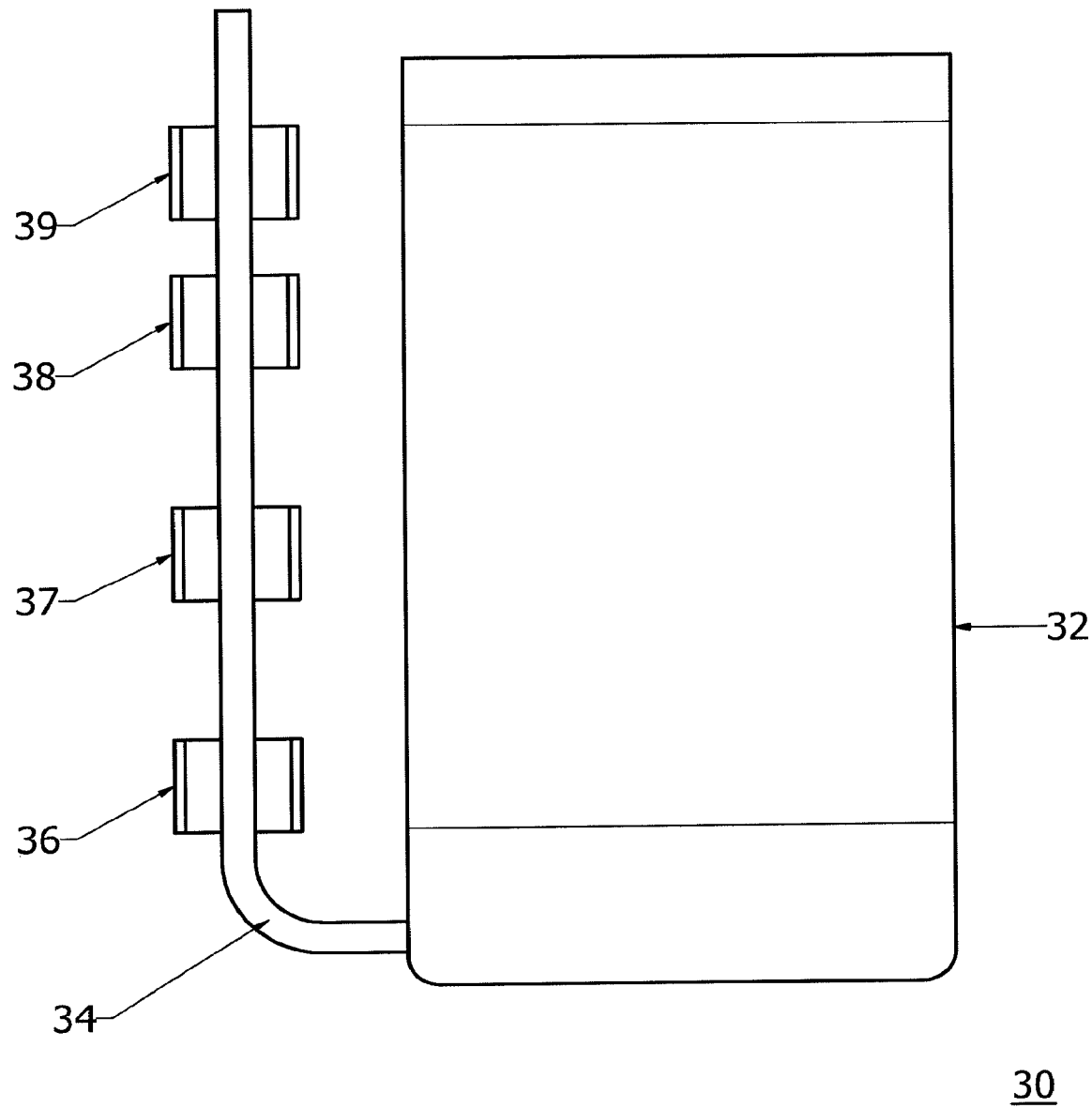
FIG. 6 illustrates the RF emitter/RF detector when utilized as a liquid level sensor.

FIG. 6 illustrates an alternate embodiment of the present invention wherein the systems and methods of the present invention are utilized for determining the level of a fluid within a tank which is shown generally at 30. In the embodiment of FIG. 6, a fluid tank 32 contains a liquid and a fluid transmission channel 34 extends vertically along a side of the fluid tank 32. A plurality of fluid level sensors 36, 37, 38, 39, are arranged at separate vertical locations along the fluid transmission channel 34. In this embodiment, changes in the detected RF signal level for each of the fluid level sensors may be used to determine a current level for the fluid within the fluid tank 32. The outputs of these signals may be transferred to logic circuitry and/or a microprocessor which may be utilized to generate a fluid level signal.

Figure 7:
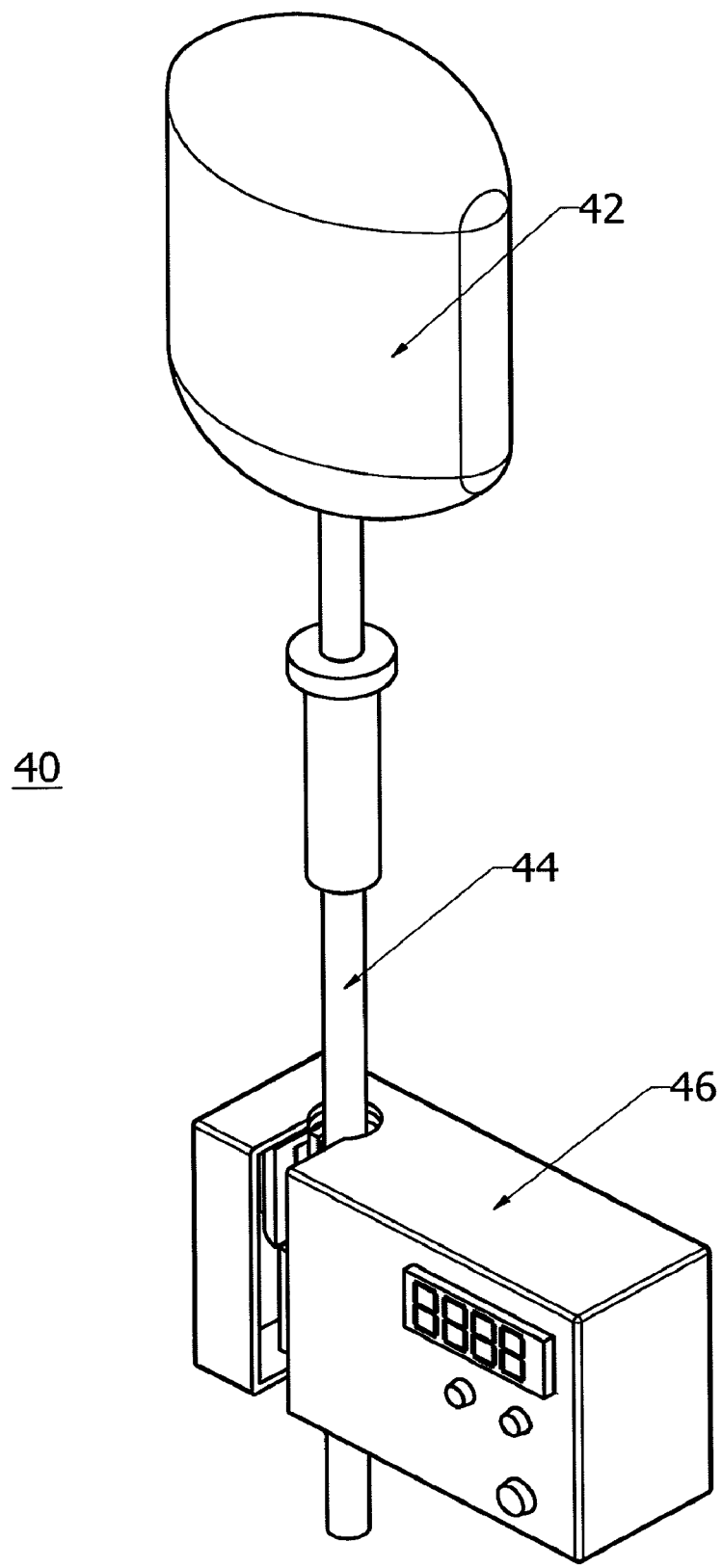
FIG. 7 illustrates use of the RF emitter and RF receiver/detector as an air bubble or contaminant sensor for an infusion system.

FIG. 7 illustrates an alternate preferred exemplary embodiment of the present invention which is shown generally at 40 wherein the systems and methods of the present invention are utilized in an intravenous fluid administration system for determining when a potentially hazardous gas bubble is present in an intravenous fluid line that is connected to a patient.

In this embodiment, an intravenous fluid source 42 is connected to a patient via an intravenous fluid transmission line 44 and a flow monitoring mechanism 46 is preferably provided for determining when a potentially harmful gas bubble is passing through the intravenous fluid line. If such an event occurs, the flow monitoring mechanism 46 also preferably incorporates an alarm and an automatic shutoff which prevents the potentially harmful gas bubble from entering a patient.

Figure 8:
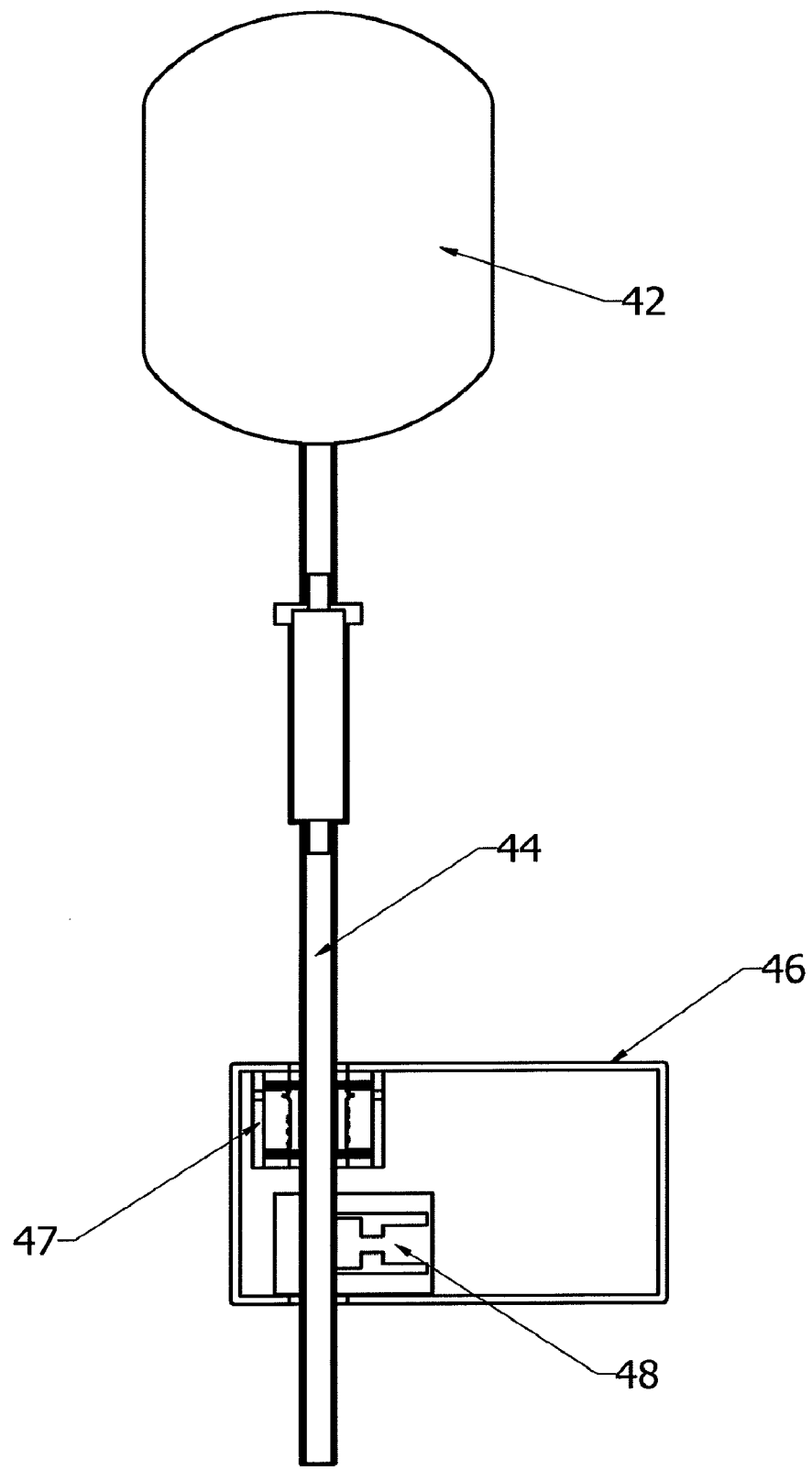
FIG. 8 is a cutaway illustration of the RF emitter and RF receiver/detector as an air bubble or contaminant sensor for an infusion system.

FIG. 8 is a cutaway view illustrating the intravenous fluid administration system shown in FIG. 7. In this embodiment, gas bubble detection circuitry 47 includes an RF energy emitter 16 and the RF energy receiver/detector 18. During system operation, a potentially harmful gas bubble may be identified by determining that gas is present in the space between the RF energy emitter 16 and the RF energy receiver/detector 18 over a sufficient period of time. It is recognized that it is not uncommon to have air bubbles in intravenous fluid administration lines, however, if they are sufficiently large, they can be hazardous to a patient. Accordingly, depending upon flow rate, the size of a potentially harmful gas bubble may be determined and if gas is present between the RF energy emitter 16 and the RF energy receiver/detector 18 over a sufficient period of time the flow shut off mechanism 48 operates to prevent the potentially harmful gas bubble from entering a patient. Either a microprocessor or logic circuitry may be utilized for generating a signal which triggers the flow shutoff mechanism 48.

Figure 9:
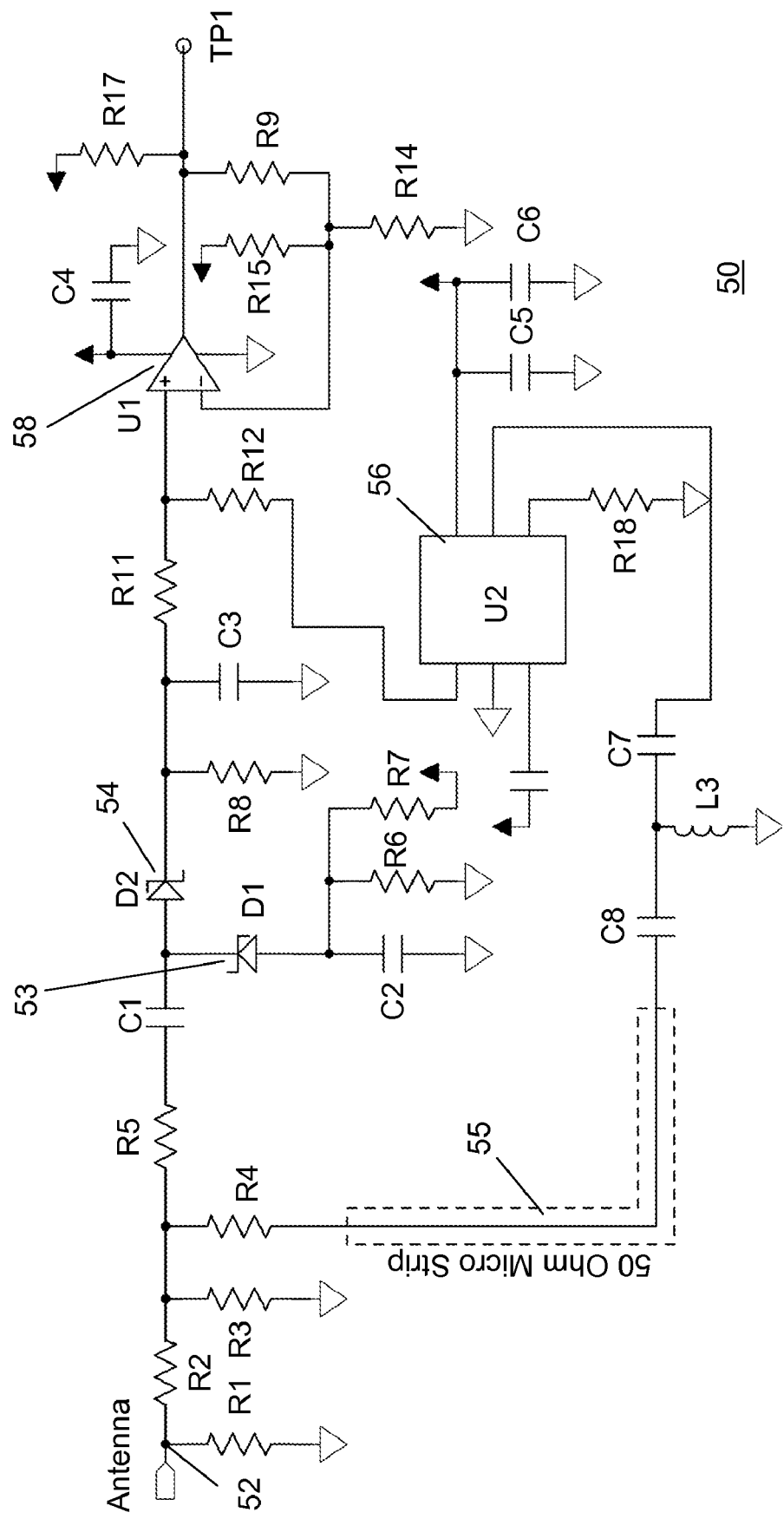
FIG. 9 is a schematic diagram which illustrates the RF detector.

FIG. 9 is a schematic diagram which illustrates a preferred circuit and arrangement for implementing the RF detector which is shown generally at 50. In accordance with the preferred exemplary embodiment as shown in FIGS. 3A-D, this circuit is preferably located on a first side of a printed circuit board and the electromagnetic energy receiver structure is preferably located on an opposite side of the printed circuit board. As noted above, antenna or electromagnetic receiver portion 25 is conveniently formed as a conductive metal layer on one side of the circuit board. In the preferred exemplary embodiment, the circuit board is preferably approximately 0.3 by 0.9 inches. The electromagnetic energy emitter or receiver portion 25 is preferably 0.3×0.7 inches. The schematic diagram illustration of FIG. 9 actually provides two alternate embodiments of the RF detector for the present invention. Antenna or electromagnetic receiver portion 25 which is not shown in this illustration is connected to the circuit at node 52.

A first embodiment employs a simple RF detector element which relies upon Schottky diodes 53, 54 which provide a DC voltage corresponding to an amount of received RF energy. Diodes D1 (53) and D2 (54) are preferably embodied as Alpha Industries model SMS7621_079. The DC voltage output from the diode D2 (54) is applied to a first input of comparator 58. A second input of comparator 58 receives a reference voltage. Those skilled in the art will appreciate that by providing an appropriate reference voltage, the comparator 58 will provide an output indicative of whether a substance is present between the RF energy emitter 16 and the RF energy receiver/detector 18.

If the diode detectors are utilized for providing the DC voltage corresponding to an amount of received RF energy, the indicated connection via the microstrip line 55 to the RF detector chip 56 is not provided. Furthermore, any of the illustrated circuitry solely relating to the operation of the RF detector chip 56 would not be provided if the Schottky diodes are utilized. Similarly, the RF detector chip 56 is not provided when the diode detectors are utilized. This first embodiment provides a less expensive alternative for determining whether a substance is present. The transmission path through the 50 ohm microstrip line 55 to the RF detector chip 56 is used as an alternate embodiment for providing more precise information. When the alternate embodiment utilizing the RF detector chip 56 is used, the connection via R 5 is not made in the diode detectors 53, 54 are not provided.

In the alternate preferred exemplary embodiment, the RF detector chip 56 is preferably an analog devices model AD8361. In this alternate embodiment, the output from the RF detector chip 56 is applied to a first input of the comparator 58. A second input of comparator 58 receives a reference voltage. Those skilled in the art will appreciate that by providing an appropriate reference voltage, the comparator 58 will provide an output indicative of whether a substance is present between the between the RF energy emitter 16 and the RF energy receiver/detector 18.

In yet another alternate arrangement, the comparator 58 may be replaced with an amplifier for applications where it is desired to achieve improved analysis of the detected RF energy. For example, when using the technology of the instant invention as a pill counter, amplification of the detected RF energy signal is required due to the brief duration of the signal pulse created when the pill passes between the RF emitter and RF receiver elements. The same is also true when utilizing the present invention for the purpose of determining an aggregate amount of bubbles passing through an intravenous fluid line. Those skilled in the art will appreciate that the specific application of the technology disclosed in the present application will determine which circuit is more appropriate.

Figure 3:
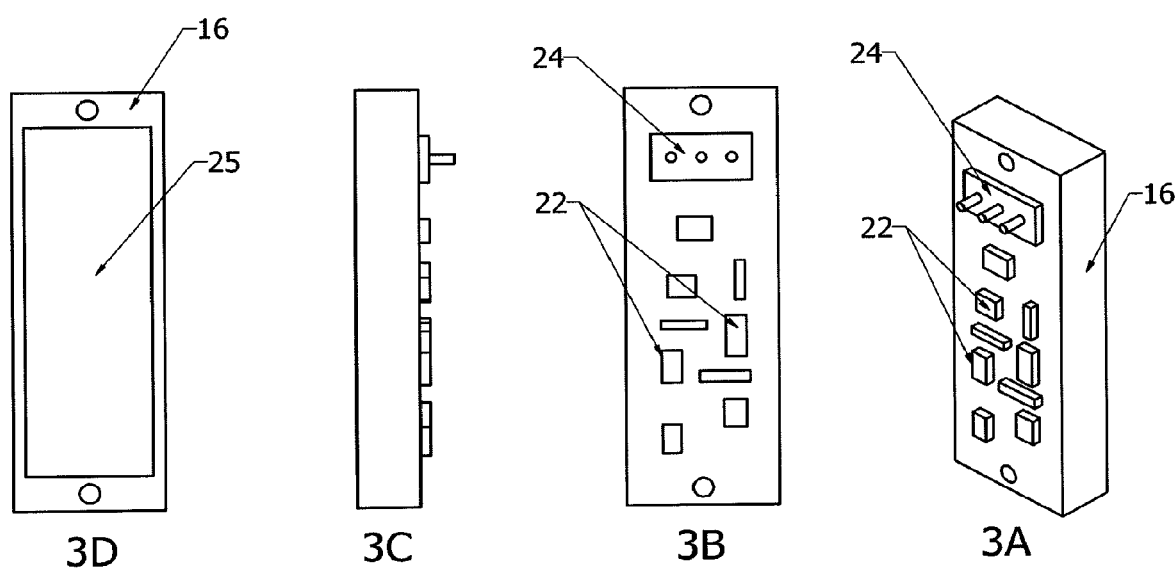
FIG. 3A illustrates a perspective view of an exemplary circuit board for use in conjunction with the present invention.
FIG. 3B illustrates a top plan view of an exemplary circuit board for use in conjunction with the present invention.
FIG. 3C illustrates a side view of an exemplary circuit board for use in conjunction with the present invention.
FIG. 3D illustrates an antenna or emitter/receiver portion provided on the printed circuit board for use in conjunction with the present invention.
Figure 10:
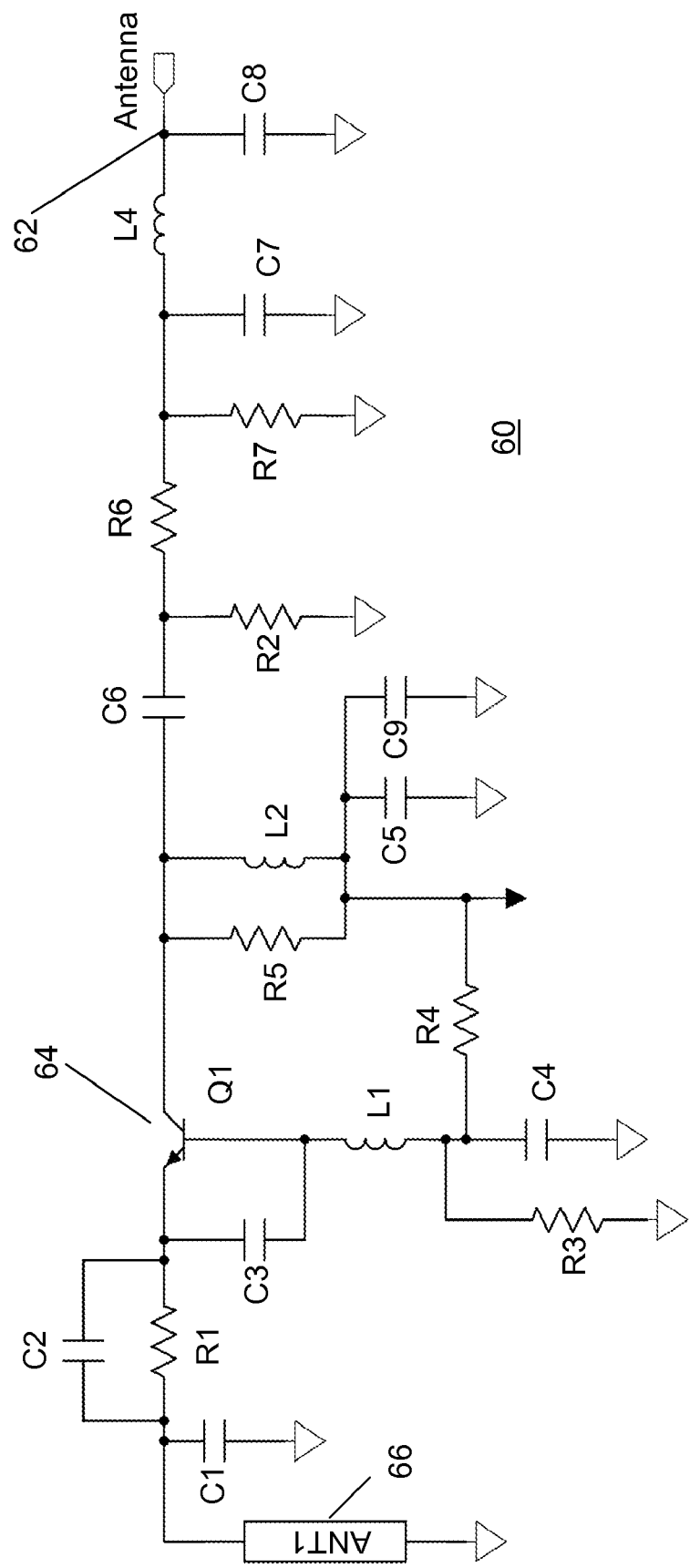
FIG. 10 is a schematic diagram which illustrates the RF emitter.

FIG. 10 illustrates an exemplary embodiment of the RF source circuitry that is shown generally at 60. In accordance with the preferred exemplary embodiment as shown in FIGS. 3 A-D, this circuit is preferably located on a first side of a printed circuit board and the electromagnetic energy emitter structure is preferably located on an opposite side of the printed circuit board. As noted above, antenna or electromagnetic emitter portion 25 is conveniently formed as a conductive metal layer on one side of the circuit board. In the preferred exemplary embodiment, the circuit board is preferably approximately 0.3 by 0.9 inches. The electromagnetic energy emitter or receiver portion 25 is preferably 0.3×0.7 inches. Antenna or electromagnetic emitter portion 25 which is not shown in this illustration is connected to the circuit at node 62.

Those skilled in the art will appreciate that a variety of different RF energy oscillator designs may be utilized. The present oscillator design is a convenient and economic alternative. In this design, a high-frequency transistor 64 embodied as a model NE68119 manufactured by Celeritek is used in generating the RF energy. Tuning of the output is achieved by altering the physical dimensions of the microstrip conductive layer 66. Various other circuit elements are provided for filtering of the output as recognized by those of ordinary skill in the art. As noted above, the preferred operating range for the RF source is in the high-frequency or ultrahigh frequency range and is preferably greater than 1 GHz and more preferably the output is at frequency range of operation around 2.4 GHz. Those skilled the art will recognize that other frequencies higher and/or lower than these ranges may also work suitably with the technology disclosed in the instant patent application.

Figure 11:
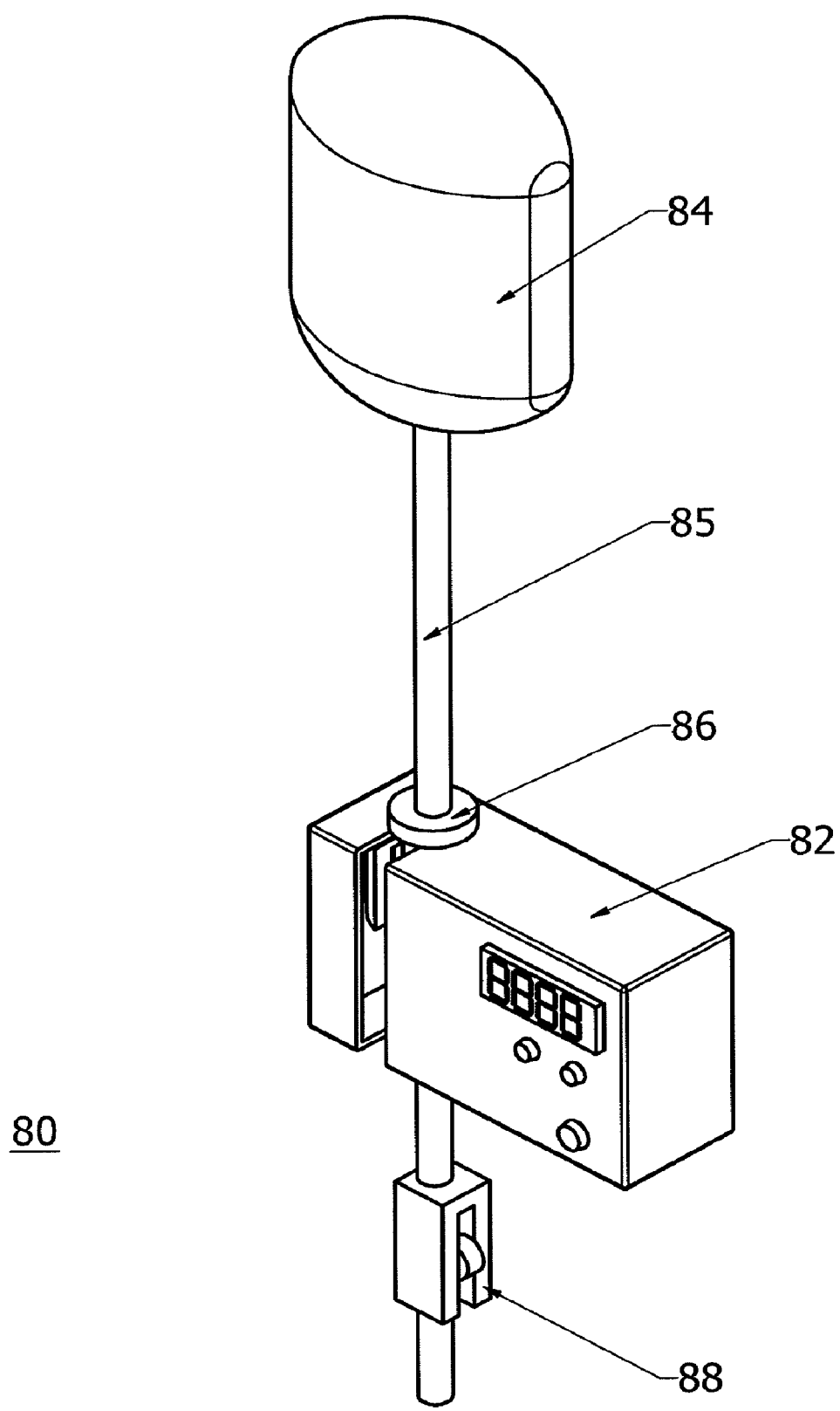
FIG. 11 illustrates use of the RF emitter and RF receiver/detector as fluid flow rate sensor embodied in an intravenous fluid system.

FIG. 11 illustrates an alternate preferred exemplary embodiment of the present invention wherein the substance detecting mechanism operates as a fluid flow rate sensor in an intravenous fluid administration system which is shown generally at 80. In this alternate preferred exemplary embodiment, the housing 82 preferably encloses the RF source and emitter structure as well as the receiving element and RF detector circuitry. An intravenous fluid source 84 is provided and an intravenous fluid line 85 transfers the intravenous fluid into the patient. The system housing 82 preferably includes a slotted region for receiving a portion of the intravenous fluid line 85 and a drip cup portion 86. A fluid flow adjustment mechanism 88 is also preferably provided.

Figure 12:
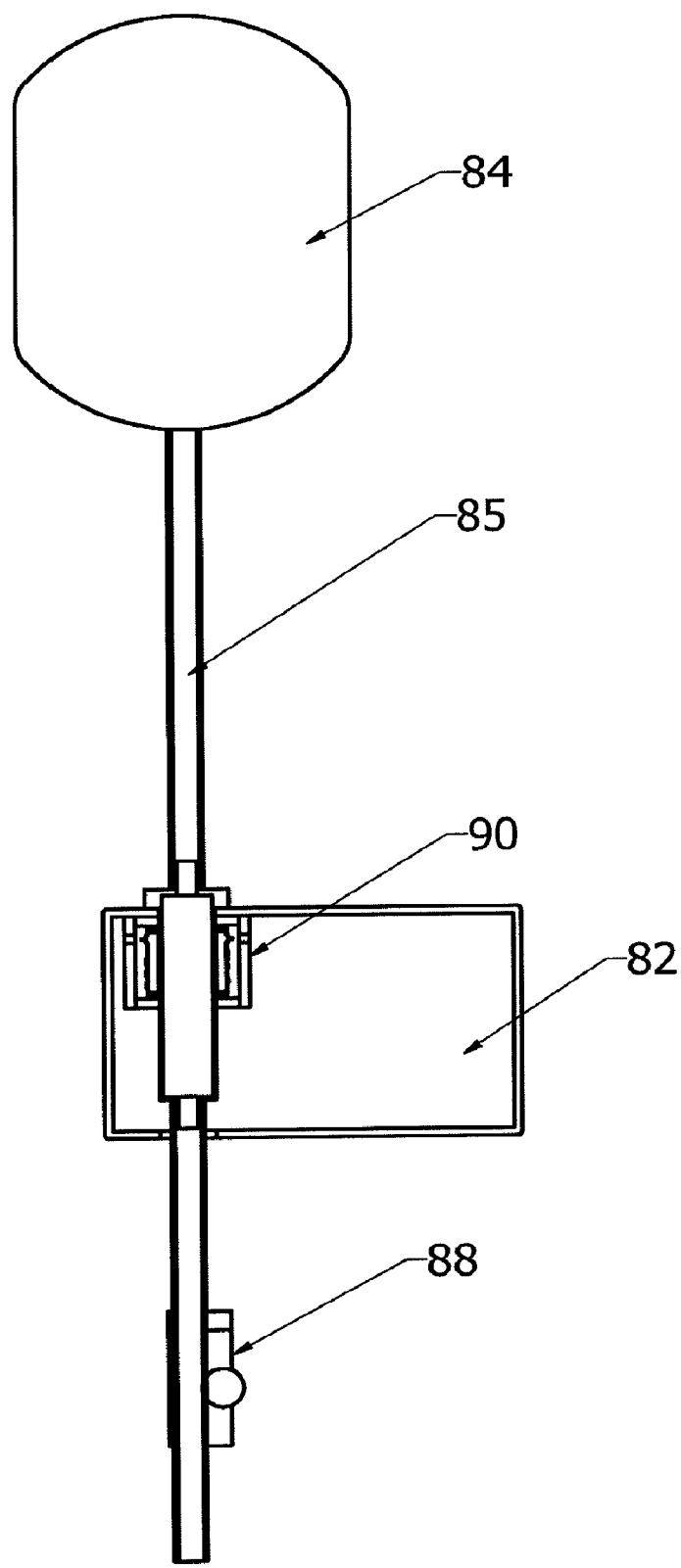
FIG. 12 is a cutaway illustration of the RF emitter and RF receiver/detector as fluid flow rate sensor embodied in an intravenous fluid system.

FIG. 12 is a cutaway illustration of the fluid flow rate sensor shown in FIG. 11. This cutaway view provides a more detailed illustration of the relationship between the source/emitter and RF receiving element/RF detector structures 16, 18 and the drip cup 86. As shown in FIG. 12, the drips of fluid traveling toward the patient pass between source/emitter and RF receiving element/RF detector structures 16, 18. The signal output corresponding to an amount of received and detected RF energy may be correlated with a fluid flow rate. For example, signal pulses or temporary rises in an output signal level indicate the passage of a drip of fluid between the RF receiving element/RF detector structures 16, 18. An amount of fluid drips passing into the drip cup in a given amount of time may be correlated with a fluid flow rate for the system. The determined fluid flow rate is preferably displayed via a liquid crystal panel. The system may incorporate alarms which indicate when a determined flow rate is not within a predetermined range of a desired fluid flow rate.

Figure 13:
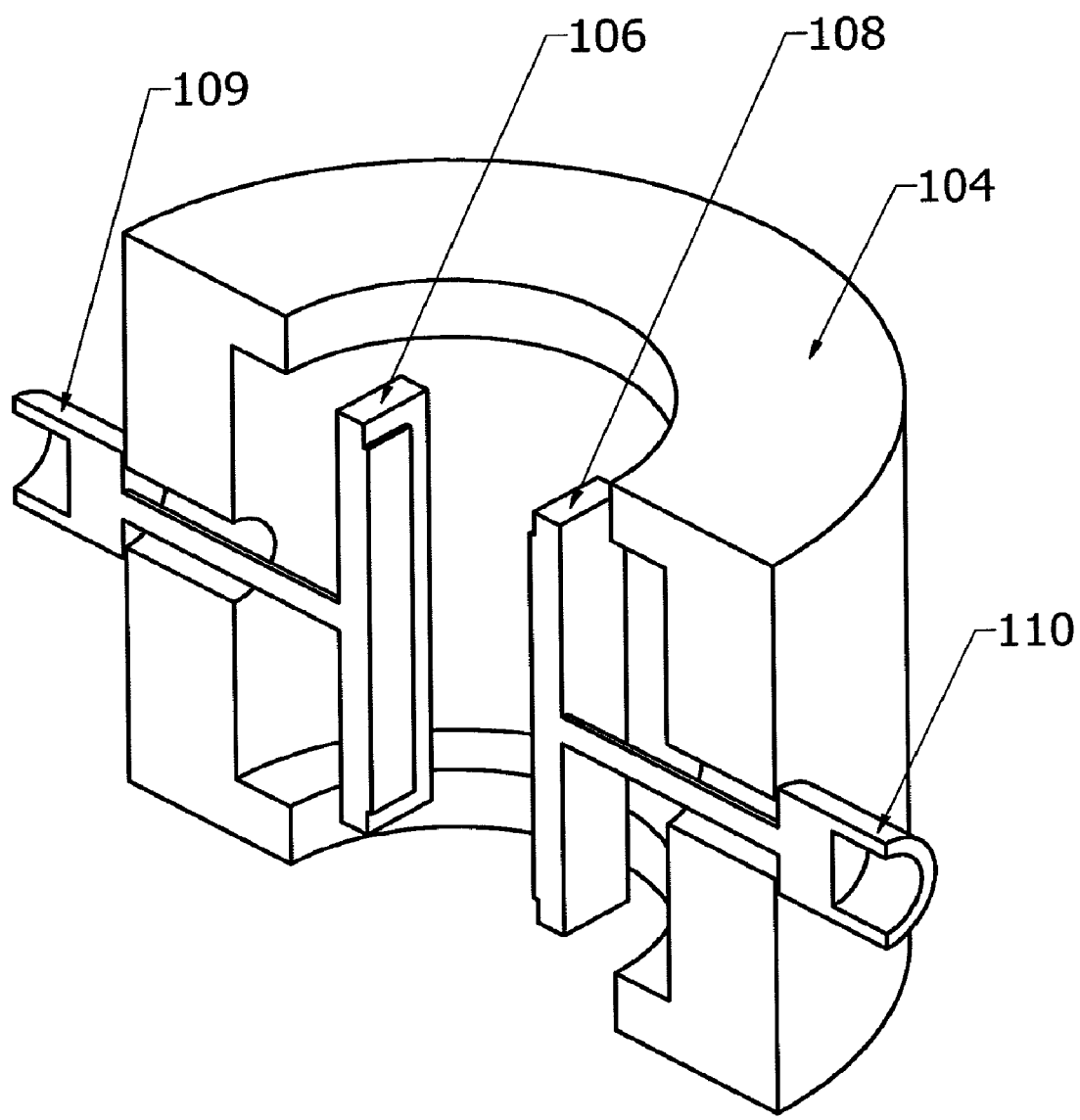
FIG. 13 illustrates the emitter and receiver structures provided on a printed circuit board for use in conjunction with the present invention wherein the RF source circuitry and RF detector circuitry are located remotely from the emitter and receiver elements.

FIG. 13 illustrates an alternate preferred exemplary embodiment of the present invention wherein the circuitry for the RF source and the RF detector are located remotely which is shown generally at 100. In this alternate preferred exemplary embodiment, a housing 104 which is preferably formed in the same manner as the housing of the embodiments described above encloses an RF emitter element 106 and an RF receiving element 108. Shielded coaxial signal lines 109 and 110 transfer the RF energy to/from the RF emitter element 106 and an RF receiving element 108. In this alternate exemplary embodiment, the circuitry for the RF source and the RF detector are located remotely from the actual location at which the substance is being detected. Those skilled in the art will appreciate that the RF emitter and receiver element structure may alternately be embodied as a single piece of a conductive material such as, for example, a conductive strip or metal wire connected to the coaxial signal lines 109 and 110 and that a printed circuit board is not required.

Figure 14:
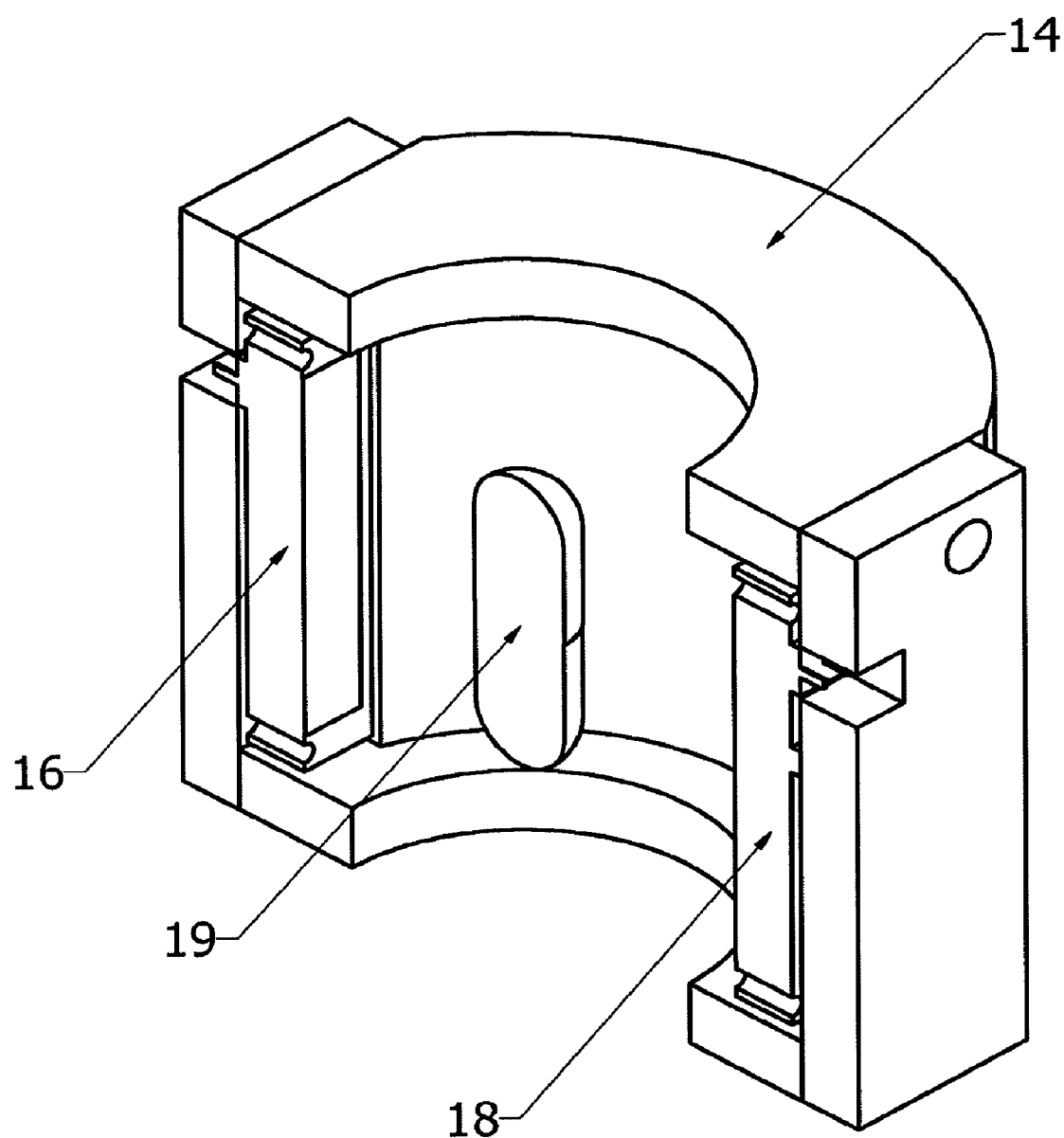
FIG. 14 illustrates the RF emitter/RF detector as a pill counter.

FIG. 14 illustrates an alternate preferred exemplary embodiment of the present invention wherein the system and methods of the present invention are used to provide either a pill counting mechanism and/or a system for verifying whether a pill or other solid object transmitted through the transmission channel is defective and/or whether it is the correct pill or other product passing through the transmission channel. As illustrated in FIG. 14, a pill 19 passes between the RF emitter and receiver element structures 16, 18. By analyzing the signal output provided by the RF detector, it is possible to determine whether a pill passing through the transmission channel is defective and/or whether the pill has a signal corresponding with a known signal for the pill.

In this alternate preferred exemplary embodiment, it is preferred that a data table or other memory construct be provided with information concerning an expected range of signals for undamaged pills or other products passing through the transmission channel between the RF emitter and receiver element structures 16, 18. This data may be generated by analysis of experimental results reviewing typical changes in the detected RF energy signal for known good pills or other products passing through the transmission channel. In this alternate embodiment, a signal corresponding to the detected amount of RF energy may be compared with a data table or other range of expected values for the signal pulse generated when the pill or other product passes through the transmission channel. If an actual detected value falls outside of a predetermined range, the system is able to determine that the pill or other product is either defective or is not the correct pill or product that was expected.

As noted above, radiating element and the receiving structure is each approximately 2 cm in length which is much smaller than the free-space wavelength of the driving RF source and they are enclosed in a small metallic RF cavity or shielded or conductive housing. Those skilled in the art will recognize that other larger or smaller radiating and receiving structures may also work suitably with the technology disclosed in the instant patent application.

The spacing between the emitter and receiving elements to the inner walls of the RF cavity is very small compare to the length of free-space wavelength of the RF driving source. Typically—but not limited to—the spacing between the radiating and receiving element is about 1 cm, which is also much smaller than the free-space wavelength of the RF driving source. Those skilled in the art will recognize that other greater or lesser spacings may also work suitably with the technology disclosed in the instant patent application.

EXAMPLES

The following examples are based on measurements using the sensor of the invention. These examples use the following values:

Operating frequency: 2.4 Ghz.
Distance r between the emitter and receiver: 1.0 cm. (0.4")
Air dielectric constant $\epsilon_O=1$.
Free space wavelength $\lambda_O=12.5$ cm.
Free space wave number $\beta_o=2\pi/\lambda_O=0.5024$.

Example 1

Distinguishing Between Air, Water and a Mixture of Water and Alcohol

A. Air: Starting with Air in the Sensor, in the Space Between the Emitter and the Receiver:

For air in the sensor $(\beta_O)(r)=(0.5024)(1)=0.5<1$, therefore with air in the sensor with this configuration the sensor is operating in the near field mode. The measured signal is 0.3 volt.

B. Water: Introduce Water in the Sensor:

Water's dielectric constant $\epsilon_w=80$. Therefore, the wavelength in water is:

$$\lambda_w=\lambda_O/\sqrt{80}=1.39 \text{ cm}.$$

Wave number in water $\beta_w = 2\pi/\lambda_w = 4.517$

Thus for water in the sensor, $(\beta_W)(r) = (4.517)(1) = 4.517 > 1$.

Therefore, when water replaces the air in the space between the emitter and the receiver with this configuration, the field mode changes from the near field to the intermediate field mode.

With water in the sensor the measured signal is 3.1 volts, an increase of a factor of ten in the measured signal over the signal with air in the space.

C. Mixture of Fluids: Change to a Mixture of Alcohol and Water:

Upstream of the sensor a T junction is connected to the sensor channel with a valve on each arm of the T junction. One arm is connected to a water reservoir and the second arm is connected to 50% water and 50% alcohol mixture reservoir. The mixture parameters are:

- Alcohol dielectric constant $\in_A = 22$
- Water dielectric constant $\in_W = 80$
- Mixture dielectric constant $\in_M = (22+80)/2 = 51$ (assuming homogeneous mixing)
- Wavelength in mixture $\lambda_M = \lambda_O/\sqrt{51} = 1.75$ cm
- Wave number in the mixture $\beta_M = 2\pi/\lambda_M = 3.58$
- For mixture in the sensor $(\beta_M)(r) = (3.58)(1) = 3.58 > 1$ Therefore for the mixture the field in the sensor with this configuration will be in intermediate field mode. (Note that the result of the mixture is estimated).

Summary:

With air in the sensor channel with the sensor in the near field in this configuration and the measured signal is about 0.3 Volt.

First we open the valve which allows water to flow through the sensor channel and with this configuration the sensor field changes from the near field to the intermediate field and the measured signal is 3.1 Volts.

We then open the valve which allows the mixture to flow through the sensor channel and close the water flow valve. With this configuration the field mode in the sensor will remain in the intermediate field but the measured signal will be an estimated 25 to 30% lower because the average dielectric constant of the mixture is lower then that of water, 51 versus 80.

Example 2

Distinguishing Between Two Immiscible Fluids

In this example, the sensor detects the presence of Kerosene in a water line. Water and kerosene do not mix, therefore kerosene will flow in the water line as kerosene and will keep its physical properties.

The Sensor parameters are:

Operating frequency: 1.5 Ghz.

Distance (r) between the emitter and receiver: 1.27 cm. (0.5")

Free space wavelength $\lambda_O = 20$

Free space wave number $\beta_o = 2\pi/\lambda_O = 0.314$.

With water in the sensor, the parameters are as follows:

Water dielectric constant $\in_W = 80$

Wavelength in water $\lambda_W = 2.23$ cm

Wave number in water $\beta_w = 2\pi/\lambda_w = 2.8$.

For water in the sensor $(\beta_W)(r) = (2.8)(1.25) = 3.5 > 1$

Therefore for water in the sensor the field mode will be the intermediate field and the measured signal will be high.

With kerosene in the sensor, the parameters would be:

Kerosene dielectric constant $\in_K = 1.8$

Wavelength in Kerosene $\lambda_K = 14.9$ cm

Wave number in Kerosene $\beta_K = 2\pi/\lambda_K = 0.421$.

For Kerosene in the sensor $(\beta_K)(r) = (0.421)(1.25) = 0.526 < 1$

Therefore for the Kerosene in the sensor the field mode in the sensor will change to the near field mode and the measured signal will be very small.

Thus, a sensor of the invention can be used to distinguish between two different immiscible liquids by detecting a mode change.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A sensor for detecting a substance within a physical space comprising:
   an RF energy signal source producing radio frequency energy having a frequency;
   an RF energy emitter on a first side of the physical space, coupled to the RF energy signal source;
   an RF energy receiving element on a second side of the physical space, spaced a determined distance from the RF energy emitter for reception of the radio frequency energy from the RF energy emitter in a near field, intermediate field or far field mode, and
   an RF energy detector providing a signal corresponding to an amount of RF energy received from the RF energy emitter;
   wherein the distance between the RF energy emitter and the RF energy receiving element is determined relative to the wavelength of the radio frequency energy in a substance such that:
      energy from the RF energy emitter is coupled to the RF energy receiving element in a selected one of near field mode, intermediate field mode or far field mode when the substance is not present in the physical space between the RF energy emitter and the RF energy receiving element, and
      energy coupled from the RF energy emitter to the RF energy receiving element changes to a different one of near field mode, intermediate field mode or far field mode when the substance is present in the physical space between the RF energy emitter and the RF energy receiving element.

2. The sensor of claim 1, further comprising a signal strength measurement circuit coupled to the signal from the RF energy detector, such that when a substance is present in the physical space such that the energy is coupled in intermediate field mode or far field mode, a signal strength representative of the substance is determined.

3. The sensor of claim 2, in which the sensor determines a change in the substance based upon a change in the signal strength measurement.

4. The sensor of claim 3, further comprising at least one stored value of signal strength related to a specific substance, and the sensor determines if a substance is the specific substance based upon a comparison of the signal strength measurement and the at least one stored value of signal strength.

5. The sensor of claim 4, in which the substance is a pill, the at least one stored value of signal strength represents a predetermined range, and the sensor determines that the pill is defective or not a correct pill if the comparison of the signal strength measurement value falls outside of the predetermined range.

6. The sensor of claim 1, further comprising a signal output having a value representative of the presence or absence of a substance in the physical space.

7. The sensor of claim 6, further comprising a counter coupled to the signal output, having a count output representative of a count of transitions from absence of substance to presence of substance and back to absence of substance, such that the count output represents a number of instances of substance passing through the sensor.

8. The sensor of claim 7, wherein the count output represents a number of solid objects passing through the physical space.

9. The sensor of claim 8, wherein the count output represents a number of solid pharmaceuticals or neutraceuticals.

10. The sensor of claim 7, wherein the count output represents a number of drops of liquid passing through the physical space.

11. The sensor of claim 10, in which the physical space is an intravenous line, and the sensor further comprises a fluid flow indicator calculating fluid flow from the number of drops over time.

12. The sensor of claim 6, further comprising an out of product indicator coupled to the signal output, in which the substance is a substance to be dispensed, and the out of product indicator is switched on when the sensor does not detect a substance in the physical space.

13. The sensor of claim 1, in which the radio frequency energy from the RF energy source is modulated on an on-off duty cycle.

14. The sensor of claim 13, in which the RF energy detector operates continuously, such that during the off time in the duty cycle, the RF energy detector measures a noise level, and during the on time in the duty cycle, the RF energy detector measures a signal plus the noise level, and by subtracting the noise level from the measured signal plus the noise level, the RF energy detector calculates a value of the signal level only.

15. The sensor of claim 1, further comprising a time measurement circuit coupled to the signal output, for timing a duration of a signal representative of no substance in the physical space.

16. The sensor of claim 15, in which the time measurement circuit further comprises an alarm output, and the alarm output is activated when a determined time of no substance is elapsed.

17. The sensor of claim 16, in which the physical space is an intravenous line, and the determined time is selected to represent a bubble in the line of determined size.

18. The sensor of claim 1, wherein the RF energy signal source and RF energy emitter are on a common circuit board.

19. The sensor of claim 1, wherein the RF energy receiving element and RF energy detector are on a common circuit board.

20. A method for detecting a substance in a physical space using an RF energy signal source producing radio frequency energy having a frequency; an RF energy emitter on a first side of the physical space, coupled to the RF energy signal source; an RF energy receiving element on a second side of the physical space, spaced a determined distance from the RF energy emitter for reception of the radio frequency energy from the RF energy emitter in a near field, intermediate field or far field mode, and an RF energy detector providing a signal corresponding to an amount of RF energy received from the RF energy emitter; the method comprising:

setting the distance between the RF energy emitter and the RF energy receiving element relative to the wavelength of the radio frequency energy in a substance such that:

energy from the RF energy emitter is coupled to the RF energy receiving element in a selected one of near field mode, intermediate field mode or far field mode when the substance is not present in the physical space between the RF energy emitter and the RF energy receiving element, and energy coupled from the RF energy emitter to the RF energy receiving element changes to a different one of near field mode, intermediate field mode or far field mode when the substance is present in the physical space between the RF energy emitter and the RF energy receiving element;

measuring the energy coupled from the RF energy emitter to the RF energy receiving element through the physical space;

determining that the substance is not in the physical space from the measured energy at a value representing coupling in one of the near field mode, intermediate field mode or far field mode; and determining that the substance is in the physical space from the measured energy at a value representing a change to coupling in a different one of near field mode, intermediate field mode or far field mode.

* * * * *